United States Patent [19]

Medero

[11] Patent Number: 5,579,776
[45] Date of Patent: Dec. 3, 1996

[54] OSCILLOMETRIC BLOOD PRESSURE MONITOR WITH ENHANCED CUFF PRESSURE CONTROL

[75] Inventor: Richard Medero, Tampa, Fla.

[73] Assignee: Johnson & Johnson Medical, Inc., New Brunswick, N.J.

[21] Appl. No.: 372,137

[22] Filed: Jan. 13, 1995

[51] Int. Cl.⁶ ..................... A61B 5/00
[52] U.S. Cl. ............. 128/680; 128/681; 128/682
[58] Field of Search ................. 128/672, 677, 128/680-3, 687

[56] References Cited

U.S. PATENT DOCUMENTS

| | | | |
|---|---|---|---|
| 4,349,034 | 9/1982 | Ramsey, III | 128/681 |
| 4,360,029 | 11/1982 | Ramsey, III | 128/681 |
| 4,461,266 | 7/1984 | Hood, Jr. et al. | 128/681 |
| 4,543,962 | 10/1985 | Medero et al. | 128/682 |
| 4,546,775 | 10/1985 | Medero | 128/681 |
| 4,627,440 | 12/1986 | Ramsey, III et al. | 128/682 |
| 4,638,810 | 1/1987 | Ramsey, III et al. | 128/681 |
| 4,754,761 | 7/1988 | Ramsey, III et al. | 128/683 |
| 4,774,960 | 10/1988 | Arnold et al. | 128/681 |
| 4,889,133 | 12/1989 | Nelson et al. | 128/681 |
| 4,926,873 | 5/1990 | Frankenreiter | 128/681 |
| 4,949,710 | 8/1990 | Dorsett et al. | 128/680 |
| 4,984,577 | 1/1991 | Frankenreiter | 128/681 |
| 5,052,397 | 10/1991 | Ramsey, III et al. | 128/682 |
| 5,054,495 | 10/1991 | Uemura et al. | 128/680 |
| 5,103,833 | 4/1992 | Apple | 128/687 |
| 5,170,795 | 12/1992 | Ramsey, III et al. | 128/682 |
| 5,218,968 | 6/1993 | Apple | 128/687 |
| 5,253,648 | 10/1993 | Walloch | 128/681 |
| 5,261,413 | 11/1993 | Kawahara | 128/682 |
| 5,280,790 | 1/1994 | Brooks | 128/681 |
| 5,311,872 | 5/1994 | Apple | 128/687 |

*Primary Examiner*—Angela D. Sykes
*Assistant Examiner*—Robert L. Nasser, Jr.
*Attorney, Agent, or Firm*—Woodcock Washburn Kurtz Mackiewicz & Norris

[57] ABSTRACT

An automated sphygmomanometer in which the so-called "air effect" (a slow rise or fall in cuff pressure caused by step inflates or deflates) is substantially eliminated by deflating (inflating) the pressure cuff to a pressure lower (higher) than the target pressure, waiting a short time interval, and then inflating (deflating) the pressure cuff to the target pressure. The driving force that causes the air effect to settle out after a step inflate or deflate is proportional to the size of the step change in pressure and is thus greatest during the wait time before the pressure cuff is inflated or deflated to the target pressure. Once at the target pressure, the remaining air effect is counteracted by the incremental air effect introduced by the latter inflate or deflate so that the air effect cancels out. The techniques of the invention provide most improved results for large inflates and deflates of 20 mm Hg or more or first deflates after a complete inflate of the pressure cuff where the air effects are most pronounced.

6 Claims, 4 Drawing Sheets

OSCILLOMETRIC BLOOD PRESSURE MONITOR WITH ENHANCED CUFF PRESSURE CONTROL

FIELD OF THE INVENTION

This invention relates to automated blood pressure monitoring, and more particularly, to automated blood pressure monitors that utilize a pneumatic cuff for accomplishing a sphygmomanometric measurement on a patient.

BACKGROUND OF THE INVENTION

The sphygmomanometric class of automated blood pressure monitors employs an inflatable cuff to exert controlled counter-pressure on the vasculature of a patient. One large class of such monitors, exemplified by that described in U.S. Pat. Nos. 4,349,034 and 4,360,029, both to Maynard Ramsey, III and commonly assigned herewith, employs the oscillometric methodology. In accordance with the Ramsey patents, an inflatable cuff is suitably located on the limb of a patient and is pumped up to a predetermined pressure above the systolic pressure. Then, the cuff pressure is reduced in predetermined decrements, and at each level, pressure fluctuations are monitored. The resultant signals typically consist of a DC voltage with a small superimposed variational component caused by arterial blood pressure pulsations (referred to herein as "oscillation complexes" or just simply "oscillations"). After suitable filtering to reject the DC component and to provide amplification, peak pulse amplitudes (PPA) above a given base-line are measured and stored. As the decrementing continues, the peak amplitudes will normally increase from a lower level to a relative maximum, and thereafter will decrease. These peak amplitudes together form an oscillometric envelope for the patient. The lowest cuff pressure at which the oscillations have a maximum value has been found to be representative of the mean arterial pressure ("MAP"). Systolic and diastolic pressures can be derived either as predetermined fractions of MAP, or by more sophisticated methods of direct processing of the oscillation complexes.

The step deflation technique as set forth in the Ramsey patents is the commercial standard of operation. A large percentage of clinically acceptable automated blood pressure monitors utilize the step deflation rationale. Accordingly, many subsequent developments have been directed at minimizing the duration of this step deflation period so as to minimize patient discomfort. For example, in U.S. Pat. No. 4,926,873 to Frankenreiter, the size of the deflation steps for a measurement cycle is varied from measurement to measurement as a function of the patient's actual blood pressure as measured in the preceding measuring cycle. This allows the duration of the measurement cycle to be minimized since extra steps can be avoided for patients with hypertension and more accurate measurements can be made for patients with hypotension. However, the duration of each deflation step within a particular measurement cycle is not varied.

On the other hand, in U.S. Pat. Nos. 4,543,962 to Medero et al., 4,889,133 to Nelson et al., and 4,949,710 to Dorsett et al., signal processing techniques are used to minimize the duration of each deflation step within a particular measurement cycle needed for detecting and processing the oscillation complexes. Such systems typically use a fixed "timeout" period at each pressure level to search for the oscillation complexes and only advance to the next step when one or more suitable oscillation complexes are detected-or the "timeout" is reached.

Unfortunately, the entire timeout period cannot be used to search for oscillation complexes because of a problem in step deflate/inflate oscillometric blood pressure monitors known as the "air effect." The "air effect" is a slow rise or fall in cuff pressure that results from a step inflate or step inflate. The air effect occurs when a quick pressure change occurs in the cuff and the pressure cannot stabilize immediately. The air effect has many different sources, such as the thermal changes in the air in the cuff as the air pressure is changed and the material properties of the cuff fabric. Generally, the air effect interferes with the small oscillations caused by the artery beneath the cuff by causing them to have modified pulse amplitudes. As a result, after a step inflate or deflate, the oscillations cannot be detected until the next heart cycle to allow time for the air effect to settle out. If the air effect is not given time to settle out, the oscillation amplitudes may be overestimated or underestimated, thereby causing errors in the blood pressure determination.

As the speed of analysis of the blood pressure envelope improves, larger deflate/inflate steps may be used to decrease the overall time for the blood pressure determination, thereby increasing the comfort to the patient. However, larger steps cause larger air effects which, in turn, cause longer determination times. As a result, the benefit of the larger steps are somewhat negated by the increased time needed at each step to detect the oscillation complexes.

It is, accordingly, a primary object of the present invention to minimize "air effects" and to shorten the time needed for air effects to settle out.

It is a further object of the present invention to prevent the underestimation or overestimation of the pulse amplitudes during an oscillometric blood pressure measurement.

It is yet another object of the present invention to minimize errors caused by "air effects" when large deflates are used between pulse measurements.

SUMMARY OF THE INVENTION

The above objects have been met in accordance with the present invention by providing an automated sphygmomanometer in which the air effect is substantially eliminated by deflating the pressure cuff to a pressure lower than the target pressure, waiting a short time interval, and then inflating the pressure cuff to the target pressure. Of course, this process is reversed for step inflates. The driving force that causes the air effect to settle out after a step inflate or deflate is proportional to the size of the step change in pressure and is thus greatest during the wait time before the pressure cuff is inflated or deflated to the target pressure. Once at the target pressure, the remaining air effect is counteracted by the incremental air effect introduced by the latter inflate or deflate so that the air effect settles out sooner or is completely eliminated.

The techniques of the invention are preferably used for large inflates and deflates of 20 mm Hg or more where the air effects are most pronounced; however, the techniques of the invention may be used for small inflates and deflates as well. The techniques of the invention may also be implemented mathematically by determining a mathematical model of the air effect, running this mathematical model concurrently with the blood pressure determination, and then arithmetically cancelling the air effect.

BRIEF DESCRIPTION OF THE DRAWINGS

The present invention will be better understood after reading the following detailed description of the presently preferred embodiments thereof with reference to the appended drawings, in which.

DETAILED DESCRIPTION OF THE PRESENTLY PREFERRED EMBODIMENT

A system and method which meets the above-mentioned objects and provides other beneficial features in accordance with the presently preferred exemplary embodiment of the invention will be described below with reference to FIGS. 1–4. Those skilled in the art will readily appreciate that the description given herein with respect to those figures is for explanatory purposes only and is not intended in any way to limit the scope of the invention. Accordingly, all questions regarding the scope of the invention should be resolved by referring to the appended claims.

In U.S. Pat. No. 4,360,029, Ramsey discloses in great detail a system for oscillometric blood pressure monitoring to which the principles of the present invention may be applied with advantage. The disclosure of the Ramsey '029 patent is incorporated by reference herein. The following description of FIG. 1 will act as a brief summary of the operation of that system.

Figure 1:
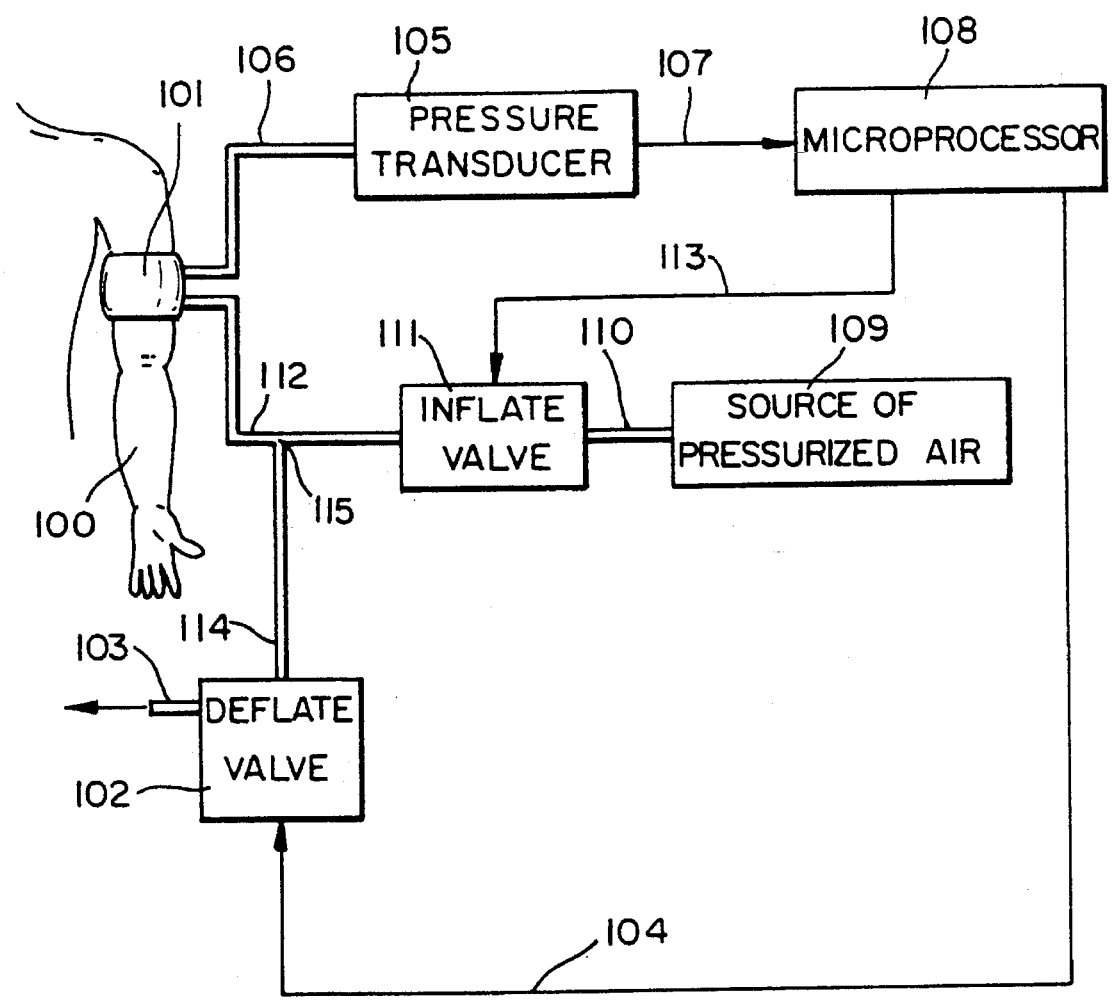
FIG. 1 is a schematic representation of a blood pressure monitor embodying the present invention.

In FIG. 1, the arm 100 of a human subject is shown wearing a conventional flexible inflatable and deflatable pressure cuff 101 for occluding the brachial artery when fully inflated. As the pressure cuff 101 is deflated using deflate valve 102 having exhaust 103, the arterial occlusion is gradually relieved. As will be described more fully below, the deflation of pressure cuff 101 via deflate valve 102 is controlled by microprocessor 108 via control line 104.

A pressure transducer 105 is coupled by a duct 106 to the pressure cuff 101 for sensing the pressure therein. In accordance with conventional oscillometric techniques, pressure oscillations in the artery are sensed by changes in the counter-pressure of the pressure cuff 101, and these pressure oscillations are converted into an electrical signal by transducer 105 and coupled over path 107 to a microprocessor 108 for processing. In addition, a source of pressurized air 109 is connected via a duct 110 through an inflate valve 111 and a duct 112 to the pressure cuff 101. The inflate valve 111 is electrically controlled through a connection 113 from the microprocessor 108. Finally, the deflate valve 102 is connected by duct 114 via a branch connection 115 with the duct 112 leading to pressure cuff 101.

From the standpoint of the principles of the present invention, the processing of the signals from pressure transducer 105 by the microprocessor 108 to produce blood pressure data, and optionally to reject artifact data, can be conducted in accordance with the prior art teachings of the above-referenced Ramsey '029 and '034 patents. Alternatively, the blood pressure can be determined in accordance with the teachings of Medero et al. in U.S. Pat. Nos. 4,543,962, of Medero in 4,546,775, of Hood, Jr. et al. in 4,461,266, of Ramsey, III et al. in 4,638,810, of Ramsey, III et al. in 4,754,761, of Ramsey, III et al. in 5,170,795, and of Ramsey, III et al. in 5,052,397, all of which are commonly assigned herewith and the disclosures of which are hereby incorporated by reference. In any event, it is desirable to use any of the known techniques to determine the quality of the oscillation complexes received at each level so that the blood pressure determination is made using actual blood pressure data and not artifacts.

The apparatus described above with reference to FIG. 1, except for the programming of the microprocessor 108, can be substantially the same as that disclosed in the Ramsey, III et al. '029 and '034 patents. Thus, during operation of the apparatus illustrated in FIG. 1, it can be assumed that air under pressure to about 8–10 p.s.i. is available in the source of pressurized air 109. When it is desired to initiate a determination of blood pressure, the microprocessor 108 furnishes a signal over path 113 to open the inflate valve 111. The deflate valve 102 is closed. Air from the source 109 is communicated through inflate valve 111 and duct 112 to inflate the pressure cuff 101 to a desired level, preferably above the estimated systolic pressure of the patient. Microprocessor 108 responds to a signal on path 107 from the pressure transducer 105, which is indicative of the instantaneous pressure in the pressure cuff 101, to interrupt the inflation of the pressure cuff 101 when the pressure in the pressure cuff 101 reaches a predetermined value above the estimated systolic pressure of the patient. Such interruption is accomplished by sending a signal over path 113 instructing inflate valve 111 to close. Once inflate valve 111 has been closed, the blood pressure measurement can be obtained by commencing the deflate routine.

As noted above, actual measurement of the blood pressure under the control of the microprocessor 108 and the deflate valve 102 as sensed by pressure transducer 105 can be accomplished in any suitable manner such as that disclosed in the aforementioned patents. At the completion of each measurement cycle, the deflate valve 102 can be reopened long enough to relax the cuff pressure substantially completely via exhaust 103. Thereafter, the deflate valve 102 is closed for the start of a new measurement cycle.

By way of a summation, when a blood pressure measurement is desired, the inflate valve 111 is opened while the cuff pressure is supervised by pressure transducer 105 until the cuff pressure reaches the desired level. The inflate valve 111 is then closed. Thereafter, the deflate valve 102 is operated using signal 104 from microprocessor 108 and the blood pressure measurement taken. To this point, the monitor operates in a conventional manner. The present invention relates to a modification of the deflation phase, and that operation will now be described with particular reference to FIGS. 2–4.

Figure 2:
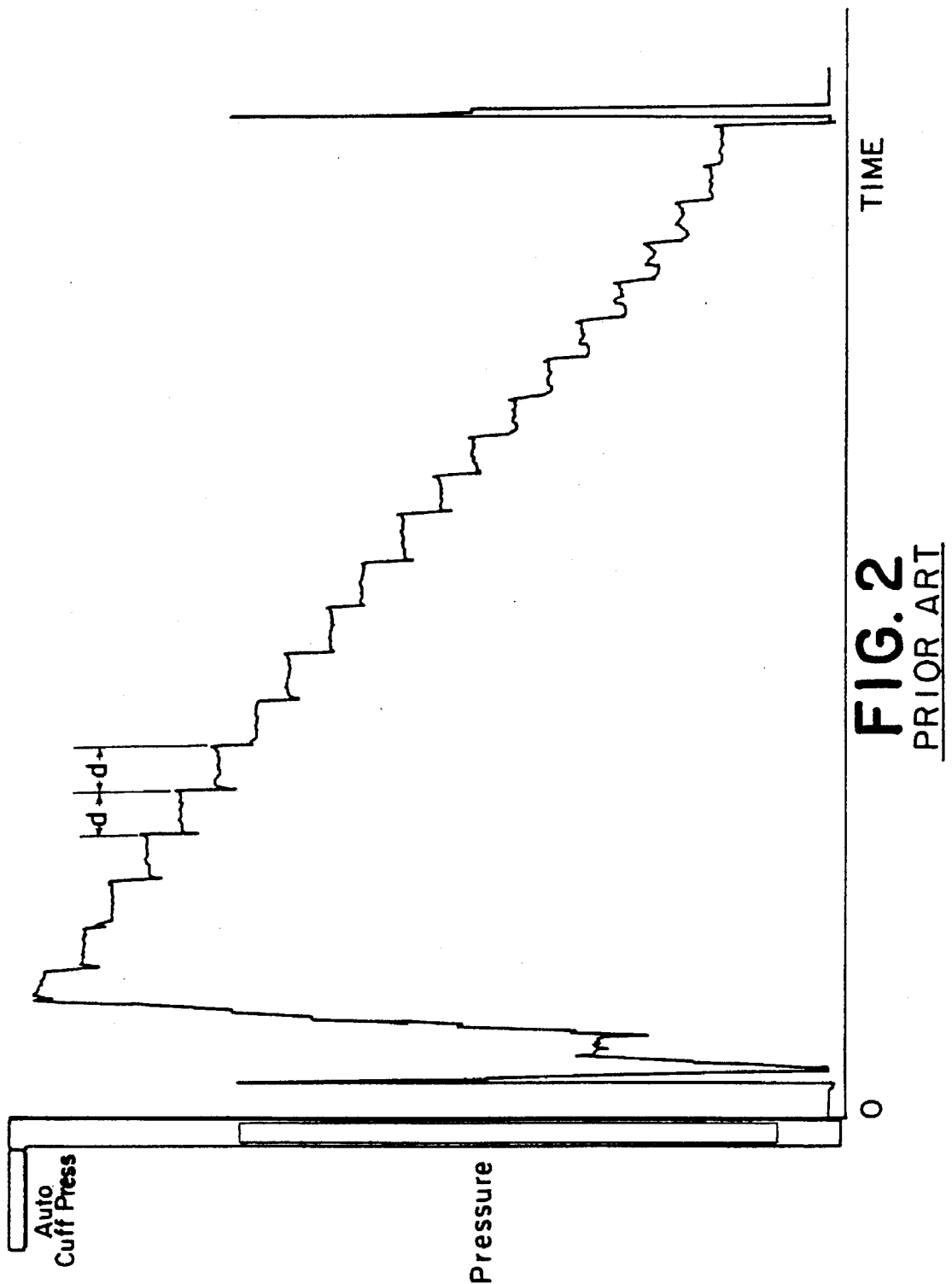
FIG. 2 is a pressure versus time graph illustrating a measuring cycle including step deflation steps as in a conventional noninvasive blood pressure measurement system.

In typical automatic sphygmomanometric devices, the cuff deflation operation is accomplished in equal decrements, usually about 8 mm Hg per step. Prior art FIG. 2 illustrates a pressure versus time graph illustrating a conventional cuff step deflation and measurement cycle for a conventional noninvasive blood pressure (NIBP) monitor. As illustrated, the pressure cuff 101 is inflated to a pressure above the systolic pressure, and the pressure cuff 101 is then deflated in steps of equal duration of about 8 mm Hg per step. A timeout duration d is provided at each step during which the signal processing circuitry searches for oscillation complexes in accordance with the techniques described in the afore-mentioned commonly assigned patents. At the end of timeout duration d, the cuff pressure is decremented even if no oscillation complex is detected. This process of decrementing the cuff pressure and searching for oscillation complexes is repeated at least until MAP and/or the oscillation envelope may be determined. The entire blood pressure determination process is then repeated at set intervals.

As noted above, the entire timeout duration d cannot be used to search for oscillation complexes because of the "air effect" which occurs when a quick pressure change occurs in the pressure cuff 101 and the pressure cannot stabilize immediately. Time must be allowed after a step inflate or deflate for the air effect to settle out before the oscillations may be detected. The time required for the step inflate to settle out increases as the step size increases. The operation of a step deflation/inflation technique for minimizing the air effect for a 20 mm Hg step size in accordance with the invention is illustrated in FIG. 3.

Figure 3:
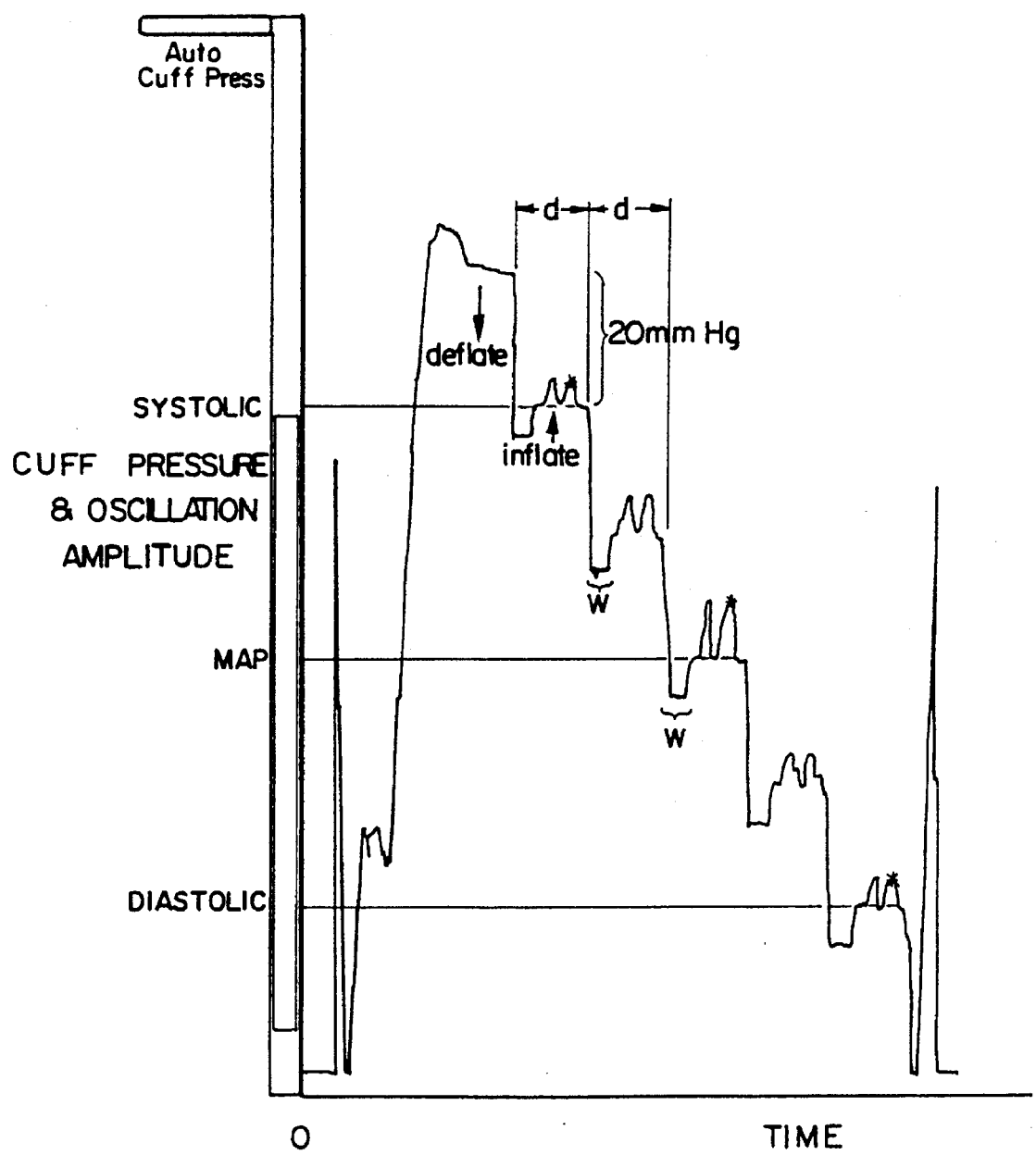
FIG. 3 is a pressure versus time graph illustrating a measuring cycle including deflation and inflation steps for negating the air effect in accordance with the techniques of the invention.

FIG. 3 is a pressure versus time graph for a blood pressure monitor modified in accordance with the principles of the invention so as to minimize the "air effect" problem which may occur in conventional blood pressure monitors. As illustrated in FIG. 3, the pressure cuff 101 is inflated to a pressure above systolic pressure and then deflated in equal decrements of about 20 mm Hg for a rapid blood pressure determination requiring relatively few samples. As shown, in accordance with the invention each step deflate does not deflate the pressure cuff 101 directly to the target pressure. Instead, for each step, the pressure cuff 101 is deflated to a pressure lower than the target pressure, a short time interval w is allowed to pass, and the pressure cuff 101 is then inflated to the target pressure. This process is reversed for step inflates. Since the driving force that causes the air effect to settle out after a step inflate or deflate is proportional to the size of the step change in pressure, the air effect is greatest during the wait time w before the pressure cuff 101 is inflated or deflated to the target pressure. Once at the target pressure, the remaining air effect is counteracted by the incremental air effect introduced by the latter inflate or deflate so that the air effect settles out sooner or is completely eliminated.

As shown in FIG. 3, the overall duration at each pressure step is still d (d>>w); however, the likelihood of an accurate measurement is greatly enhanced by the cancellation of the air effect. Also, the duration of w is preferably kept short to minimize the length of duration d at each pressure step.

Figure 4:
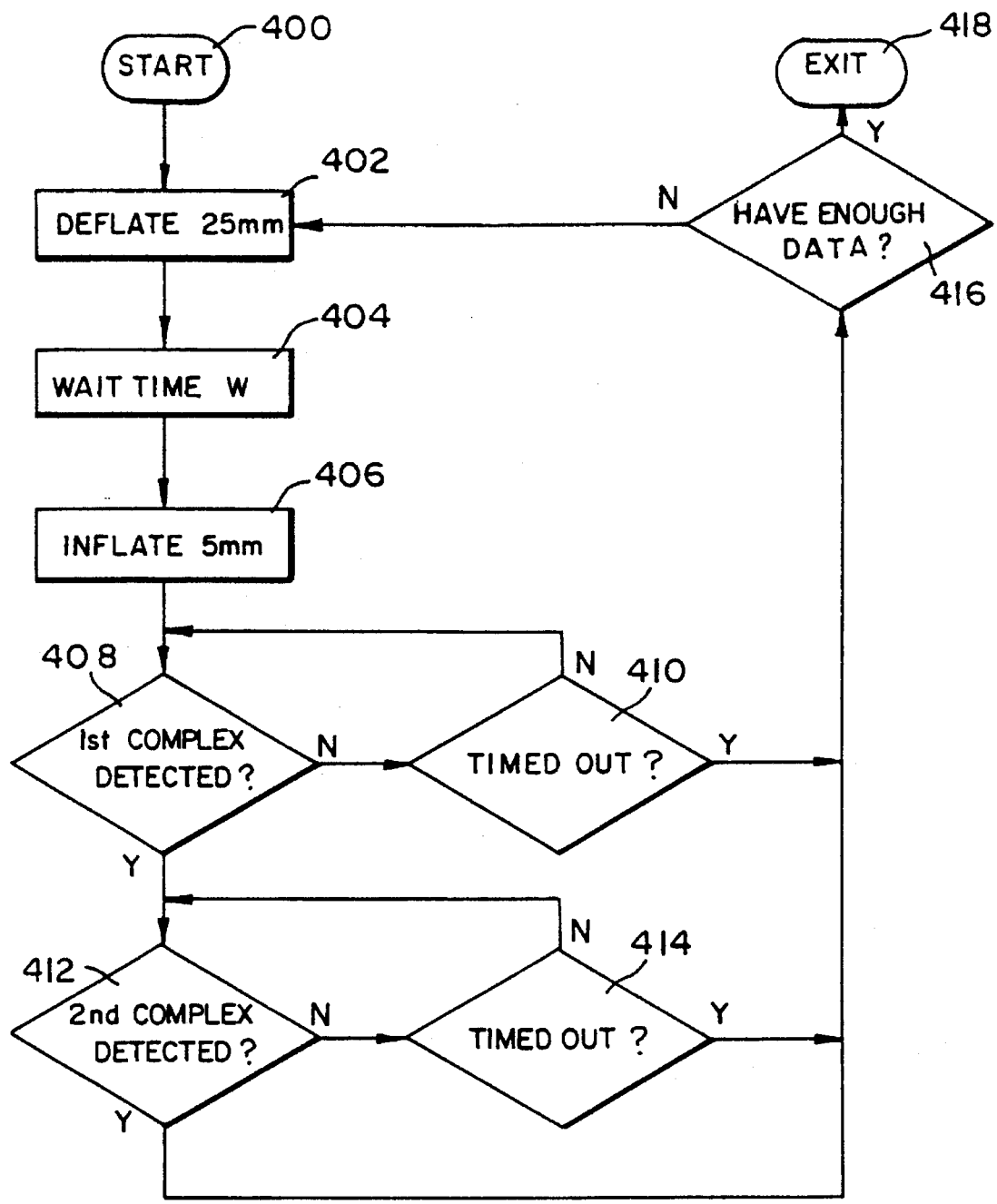
FIG. 4 is a flow chart representing the operation of the apparatus of FIG. 1 under control of a microprocessor programmed to overshoot on the deflate and then inflate to the target pressure in accordance with the techniques of the invention.

The operation of the present invention will now be described with reference to the flow chart of FIG. 4. Those skilled in the art will appreciate that the flow chart of FIG. 4 is typically implemented in software on microprocessor 108 of FIG. 1 for controlling the step deflation cycle.

At the commencement of the deflation operation at step 400, pressure cuff 101 is deflated at step 402 by pressure increments of a predetermined fixed magnitude, generally about 25 mm Hg per step for a desired deflation of 20 mm Hg per step, by opening deflation valve 102. At step 404, the system waits for a short duration w (d>>w) for allowing the air effect to somewhat settle out. Then, at step 406, inflate valve 111 is opened to inflate pressure cuff 101 by about 5 mm Hg so that the overall step deflate is –20 mm Hg (–25 mm Hg+5 mm Hg). The system then checks for oscillation complexes at the present pressure level at step 408 using conventional procedures described in the aforementioned commonly owned patents. If no oscillation complexes are detected at step 408, the system continues to check for an oscillation complex until the end of the timeout duration is reached at step 410. At this time, processing proceeds to step 416 where it is determined whether enough data has been collected to determine the patient's blood pressure. If enough data has been collected, the deflation routine is exited at step 418. However, if enough data has not been collected, steps 402–406 are repeated so that the pressure cuff 101 is again deflated 20 mm Hg to the next deflation step.

If an oscillation complex is detected at step 408, the system then searches for a second oscillation complex at step 412 until the end of the timeout duration is reached at step 414. At this time, processing proceeds to step 416 where it is determined whether enough data has been collected to determine the patient's blood pressure. If enough data has been collected, the deflation routine is exited at step 418. However, if enough data has not been collected, steps 402–406 are repeated so that the pressure cuff 101 is again deflated 20 mm Hg to the next deflation step.

Generally, the amplitude of the two oscillation complexes detected at steps 408 and 412 at each pressure level are compared to determine if they are of sufficient quality, as described by Ramsey et al. in the aforementioned '029 and '034 patents. Once it is determined at step 416 that enough data to define the blood pressure envelope has been detected, the deflation routine is exited at step 418 for a blood pressure determination.

The techniques of the invention are preferably used for large inflates and deflates of 20 mm Hg or more or in the first steps after inflation where the air effects are most pronounced; however, the techniques of the invention may be used for small inflates and deflates as well, such as conventional deflates on the order of 8 mm Hg. The techniques of the invention may also be implemented mathematically by determining a mathematical model of the air effect, running this mathematical model concurrently with the blood pressure determination, and then arithmetically cancelling the air effect.

It will be appreciated by those skilled in the art that the foregoing has set forth the presently preferred embodiment of the invention and an illustrative embodiment of the invention but that numerous alternative embodiments are possible without departing from the novel teachings of the invention. For example, those skilled in the art will appreciate that the techniques of the invention may be used for blood pressure monitors in which the pressure is incremented from diastolic as described, for example, in U.S. Pat. No. 4,461,266 to Hood, Jr. et al. Also, those skilled in the art will appreciate that the techniques of the invention may be used for blood pressure monitors which do not use amplitude matching techniques described by Ramsey to determine whether oscillation complexes of sufficient quality have been received. In addition, those skilled in the art will appreciate that the techniques of the invention may be expanded to permit multiple, possibly somewhat random, timeout durations for the measurements at respective deflation levels. Accordingly, all such modifications are intended to be included within the scope of the appended claims.

I claim:

1. An automated sphygmomanometer apparatus, comprising:

an inflatable and deflatable pressure cuff;

inflating means operatively coupled to said cuff for selectively applying a medium under pressure to said cuff for inflating and pressurizing said cuff;

cuff pressure sensing means coupled to said cuff for sensing cuff pressure including any blood pressure oscillations therein;

deflating means operatively coupled to said cuff for selectively relieving pressure from said cuff; and control means for measuring a patient's blood pressure from a cuff pressure sensed by said cuff pressure sensing means, said control means controlling said inflating means to inflate said cuff and said deflating means to deflate said cuff during a blood pressure measurement of said patient, said control means instructing said inflating means to inflate said cuff to a predetermined pressure above an estimated systolic pressure of said patient at a beginning of a blood pressure measurement cycle, instructing said deflating means to deflate said cuff in pressure steps to respective pressures lower than respective target pressures and, after predetermined intervals of time, instructing said inflating means to inflate said cuff to said respective target pressures for a determination of the existence and magnitude of blood pressure oscillations at each of said respective target pressures by said cuff pressure sensing means.

2. An automated sphygmomanometer apparatus, comprising:

an inflatable and deflatable pressure cuff;

inflating means operatively coupled to said cuff for selectively applying a medium under pressure to said cuff for inflating and pressurizing said cuff;

cuff pressure sensing means coupled to said cuff for sensing cuff pressure including any blood pressure oscillations therein;

deflating means operatively coupled to said cuff for relieving pressure from said cuff; and control means for measuring a patient's blood pressure from a cuff pressure sensed by said cuff pressure sensing means, said control means controlling said inflating means to inflate said cuff and said deflating means to deflate said cuff during a blood pressure measurement of said patient, said control means instructing said inflating means during a blood pressure measurement cycle to inflate said cuff in pressure steps to respective pressures above respective target pressures, and, after predetermined intervals of time, instructing said deflating means to deflate said cuff to said respective target pressures for a determination of the existence and magnitude of blood pressure oscillations at each of said respective target pressures by said cuff pressure sensing means.

3. A method of measuring blood pressure of a patient using an automatic oscillometric blood pressure monitor comprising a pressurized cuff, means for inflating and deflating said cuff in pressure steps to respective pressure levels during a blood pressure measurement, and means for measuring arterial pressure oscillation complexes at said respective pressure levels through measurement of time varying pressures within said cuff, said method comprising the steps of:

(a) inflating said cuff about an artery of the patient until said cuff is at a first pressure level a predetermined amount above the patient's estimated systolic pressure;

(b) deflating said cuff from said first pressure level to a second pressure level below a target pressure level;

(c) after a predetermined interval of time, inflating said cuff from said second pressure level to said target pressure level;

(d) searching for arterial pressure oscillation complexes at said target pressure level; and (e) repeating steps (b)–(d) for subsequent blood pressure levels during said blood pressure measurement until arterial pressure oscillation complexes of a predetermined quality are detected in step (d) for a sufficient number of pressure levels to permit a blood pressure determination for the patient.

4. A method of measuring blood pressure of a patient using an automatic oscillometric blood pressure monitor comprising a pressurized cuff, means for inflating and deflating said cuff in pressure steps to respective pressure levels during a blood pressure measurement, and means for measuring arterial pressure oscillation complexes at said respective pressure levels through measurement of time varying pressures within said cuff, said method comprising the steps of:

(a) inflating said cuff about an artery of the patient until said cuff is at a first pressure level a predetermined amount above a target pressure level;

(b) after a predetermined interval of time, deflating said cuff from said first pressure level to said target pressure level;

(c) searching for arterial pressure oscillation complexes at said target pressure level; and (d) repeating steps (a)–(c) for higher target pressure levels during said blood pressure measurement until arterial pressure oscillation complexes of a predetermined quality are detected in step (c) for a sufficient number of pressure levels to permit a blood pressure determination for the patient.

5. An automated sphygmomanometer apparatus, comprising:

an inflatable and deflatable pressure cuff;

inflating means operatively coupled to said cuff for selectively applying a medium under pressure to said cuff for inflating and pressurizing said cuff;

cuff pressure sensing means coupled to said cuff for sensing cuff pressure including any blood pressure oscillations therein;

deflating means operatively coupled to said cuff for relieving pressure from said cuff; and control means for measuring a patient's blood pressure from a cuff pressure sensed by said cuff pressure sensing means, said control means controlling said inflating means to inflate said cuff and said deflating means to deflate said cuff during a blood pressure measurement of said patient, said control means instructing said inflating means and said deflating means during a blood pressure measurement cycle to inflate/deflate said cuff in pressure steps to respective pressures beyond respective target pressures in a direction of inflation/deflation and, after predetermined intervals of time, instructing said deflating means and said inflating means to deflate/inflate said cuff back to said respective target pressures for a determination of the existence and magnitude of blood pressure oscillations at each of said respective target pressures by said cuff pressure sensing means.

6. A method of measuring blood pressure of a patient using an automatic oscillometric blood pressure monitor comprising a pressurized cuff, means for inflating and deflating said cuff in pressure steps to respective pressure levels during a blood pressure measurement, and means for measuring arterial pressure oscillation complexes at said respective pressure levels through measurement of time varying pressures within said cuff, said method comprising the steps of:

(a) inflating/deflating said cuff about an artery of the patient until said cuff is at a first pressure level a predetermined amount beyond a target pressure level in a direction of inflation/deflation;

(b) after a predetermined interval of time, deflating/inflating said cuff from said first pressure level back to said target pressure level;

(c) searching for arterial pressure oscillation complexes at said target pressure level; and (d) repeating steps (a)–(c) for respective target pressure levels during said blood pressure measurement until arterial pressure oscillation complexes of a predetermined quality are detected in step (c) for a sufficient number of pressure levels to permit a blood pressure determination for the patient.

* * * * *